United States Patent [19]

Fordenbacher

[11] Patent Number: 5,733,328
[45] Date of Patent: *Mar. 31, 1998

[54] EXPANDABLE STENT USING SLIDING MEMBERS

[75] Inventor: Paul J. Fordenbacher, Minneapolis, Minn.

[73] Assignee: SciMed Life Systems, Inc., Maple Grove, Minn.

[*] Notice: The portion of the term of this patent subsequent to Nov. 7, 2014, has been disclaimed.

[21] Appl. No.: 670,575

[22] Filed: Jun. 26, 1996

Related U.S. Application Data

[63] Continuation of Ser. No. 335,316, Nov. 7, 1994, Pat. No. 5,549,662.

[51] Int. Cl.$^6$ .............................. A61F 2/06; A61M 29/00
[52] U.S. Cl. ................................. 623/1; 606/198
[58] Field of Search ...................... 606/198, 191; 623/1, 12

[56] References Cited

U.S. PATENT DOCUMENTS

| | | |
|---|---|---|
| 4,733,665 | 3/1988 | Palmaz . |
| 4,740,207 | 4/1988 | Kreamer . |
| 4,994,071 | 2/1991 | MacGregor . |
| 5,007,926 | 4/1991 | Derbyshire . |
| 5,041,126 | 8/1991 | Gianturco . |
| 5,192,307 | 3/1993 | Wall . |
| 5,236,447 | 8/1993 | Kubo et al. . |
| 5,266,073 | 11/1993 | Wall . |
| 5,306,286 | 4/1994 | Stack et al. . |
| 5,344,426 | 9/1994 | Lau et al. . |
| 5,354,309 | 10/1994 | Schnepp-Pesch et al. . |
| 5,383,926 | 1/1995 | Lock et al. . |
| 5,421,955 | 6/1995 | Lau et al. . |
| 5,443,458 | 8/1995 | Eury . |
| 5,556,413 | 9/1996 | Lam ........................ 606/198 |

FOREIGN PATENT DOCUMENTS

| | | |
|---|---|---|
| 2008312 | 7/1990 | Canada . |
| 0382014A1 | 8/1990 | European Pat. Off. . |

OTHER PUBLICATIONS

Publication: "Intravascular Stents to Prevent Occlusion and Restenosis After Transluminal Angiop;lasty", New England Journal of Medicine, vol. 316, No. 12, Mar. 19, 1987, pp. 701–706.

*Primary Examiner*—Michael Buiz
*Assistant Examiner*—Nancy Mulcare
*Attorney, Agent, or Firm*—Vidas, Arrett & Steinkraus, P.A.

[57] ABSTRACT

The present invention provides a lumen support device, or a stent, used to open or expand a body lumen. The stent incorporates elongated parallel stent components with circumferential members, fingers, which weave into paired slots of an adjacent stent component. This weave-like interlocking configuration enables the stent to expand radially without yielding or plastically deforming the material of which the stent is fabricated. The weave-like mechanism allows for uniform, smooth expansion without change in longitudinal dimensions of the complete assembly. Once assembled, the plurality of parallel elongated stent components form a cylindrical configuration. The invention provides a stent able to support body lumens and adapt to curves or irregularities in body lumens without losing its formation or its longitudinal dimensions. It is designed to permit flexing both radially and longitudinally to conform to the curved body of the applicable lumen. The device is delivered using a percutaneous transluminal catheter device which may incorporate an inflatable balloon, self-expanding material or both to expand the stent.

10 Claims, 4 Drawing Sheets

EXPANDABLE STENT USING SLIDING MEMBERS

This application is a continuation of application Ser. No. 08/335,316, filed Nov. 7, 1994, now U.S. Pat. No. 5,549,662.

BACKGROUND OF THE INVENTION

This invention relates to intraluminal stent implants for maintaining support of a body lumen. It comprises an improvement and alternate design to stents which are generally cylindrical in shape and have a plurality of metal elements joined to permit flexing of the stent along the longitudinal axis allowing it to conform to the curves of the inner wall of the targeted lumen.

An important use of metal stents is found in situations where part of the vessel wall or stenotic plaque blocks or occludes blood flow in the vessel. Normally a balloon catheter is utilized in a percutaneous transluminal coronary angioplasty (PTCA) procedure to enlarge the occluded portion of the vessel. However, the dilation of the occlusion can form flaps, fissures and dissections which threaten re-closure of the dilated vessel or even perforations in the vessel wall. Implantation of stents can provide support for such problems and prevent reclosure of the vessel or provide patch repair for a perforated vessel. The stent overcomes the natural tenancy of the vessel walls of some patients to collapse, thereby maintaining a more normal flow of blood through that vessel than would be possible if the stent were not in place.

An example of prior developed metal stents has been described in the article of Stignart, et al. titled "Intravascular Stents To prevent Occlusion and Restenosis after Transluminal Angioplasty", published in the *New England Journal of Medicine*, Vol. 316, No. 12, Mar. 19, 1981, pages 701–706. This stent is the form of a "Chinese finger handcuff" metallic mesh which can be expanded and compressed in diameter. The stent is made by cutting desired lengths from an elongated tube of metal mesh and, accordingly, has the disadvantage that metal prongs from the cutting process remain at the longitudinal ends thereof. The inherent rigidity of the metal used to form the stent together with these terminal prongs make navigation of the blood vessels to the locus of the lesion difficult as well as risky from the standpoint of injury to healthy tissue along the passage to the target vessel. When the stent is permanently placed in a vessel, the continuous stress from the flow of the fluid within the vessel could cause the prongs to damage the vessel walls adjacent to the lesion.

Another type of metal stent involves a tube of stainless wire braid. During insertion, the tube is positioned along a delivery device, such as a catheter, in extended form, making the tube diameter as small as possible. When the stent is positioned across the lesion, it is expanded, causing the length of the tube to contract and the diameter to expand. Depending on the materials used in construction of the stent, the tube maintains the new shape either through mechanical force or otherwise. The alteration in the length is undesirable due to the deformation of the stent, the longitudinal abrasion on the inner wall and the unpredictable coverage when fully in place.

An additional form of metal stent is a heat expandable device using Nitinol or a tin-coated, heat expandable coil. The stent is delivered to the affected area on a catheter capable of receiving heated fluids. Once properly situated, heated saline is passed through the portion of the catheter on which the stent is located, causing the stent to expand. Numerous difficulties have been encountered with this device, including difficulty in obtaining reliable expansion, and difficulties in maintaining the stent in its expanded state.

A popular metal stent is the Palmaz stent. It involves a stainless steel cylinder having a number of slits in its circumference, resulting in a mesh when expanded. The stainless steel cylinder is delivered to the affected area by means of a balloon catheter, and is then expanded to the proper size.

Stents can be deployed in a body lumen by means appropriate to their design. One such method would be to fit the collapsed stent over an inflatable element of a balloon catheter and expand the balloon to force the stent into contact with the body lumen. As the balloon is inflated, the problem material in the vessel is compressed in a direction generally perpendicular to the wall of the vessel which, consequently, dilates the vessel to facilitate blood flow therethrough. Radial expansion of the coronary artery occurs in several different dimensions and is related to the nature of the plaque. Soft, fatty plaque deposits are flattened by the balloon and hardened deposits are cracked and split to enlarge the lumen. It is desirable to have the stent radially expand in an uniform manner.

Alternatively, the stent may be mounted onto a catheter which holds the stent as it is delivered through the body lumen and then releases the stent and allows it to expand into contact with the body lumen. This deployment is effected after the stent has been introduced percutaneously, transported transluminally and positioned at a desired location by means of the catheter.

It is desirable to provide a stent that has sufficient structural integrity to be placed within a vessel at the site of a stenotic lesion, or the like, to support the vessel wall against collapse and yet is flexible and compliant enough for safe and effective delivery to the site of an obstruction. It would also be desirable to provide a stent which is soft and compliant enough to avoid arterial rupture or aneurysm formation at the ends of the stent even when exposed to continuous stresses from the beating heart during chronic implantation.

Significant difficulties have been encountered with all prior art stents. Each has its percentage of thrombosis, restenosis and tissue in-growth, as well as varying degrees of difficulty in deployment. Another difficulty with at least some of prior art stents is that they do not readily conform to the vessel shape. The relatively long length of some prior art stents has made it difficult to treat curved vessels, and has also effectively prevented successful implantation of multiple such stents. Stents illustrated in the prior art tend to go through plastic deformation during expansion and as a result the expansion device does not expand uniformly to the shape of the targeted lumen. Thus there is a need for an effective stent that maintains an open vessel, is easily delivered to the affected area, one that is easily expanded to a desired size, and maintains that size, easily conforms to the shape of the effected vessel, and is easily used in multiples to treat curved vessels and varying lengths of lesions. The stent should not alter in length during expansion or incorporate plastic deformation during such uniform expansion.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

SUMMARY OF THE INVENTION

The present invention provides a lumen support device, or a stent, used to open or expand a body lumen. The stent incorporates elongated parallel stent components with circumferential members, fingers, which weave into paired slots of an adjacent stent component. The stent incorporates these sliding elements, that is these projections or fingers, such that they slide through paired slots in a weave-like interlocking configuration enabling the stent to expand radially without yielding or plastically deforming the material of which the stent is fabricated. A series of paired slots allow for the insertion of a series of the fingers. The fingers may utilize an arresting mechanism giving a controlled expansion with little or no recoil or collapse. The slots also allow for uniform, smooth expansion without change in longitudinal dimensions of the complete assembly. Once assembled, the plurality of parallel elongated stent components form a cylindrical configuration. The assembly is compressed radially by fully sliding the fingers through the slots. The assembly is expanded with either the help of a balloon catheter, by the material's elastic response, or both.

A stent formed in accordance with the present invention is expandable from a reduced diameter configuration, which facilitates delivery to the site of a targeted obstruction, to an expanded configuration when disposed within the targeted area of the vessel. The device is delivered using a percutaneous transluminal catheter device which may or may not incorporate an inflatable balloon used to expand the stent. Delivered to the locus of a lesion in its reduced diameter configuration on the distal end of an expandable catheter, the stent can be expanded in vivo to its supporting diameter by expanding the expandable portion of its associated catheter. The expansion may be accomplished through a balloon catheter or by using self-expanding material, the weave-like fingers being withdrawn through the paired slot to an arrested position. Any plaque or the like can be compressed at the time of stent placement. The features of this invention make it possible to provide a stent able to support body lumens and conform to curves or irregularities in body lumens without losing its formation or its longitudinal dimensions.

It is an object of the present invention to provide a stent having longitudinal flexibility which allows it to conform to curves and variations in body lumens.

It is another object of the invention to allow stent expansion without incorporating plastic deformation.

It is also an object of the invention to prevent change in length during radial expansion of the stent.

It is a further object of the present invention to provide a stent capable of being implanted simply and reliably.

Yet another object of the present invention is to provide a stent which can be selectively sized in accordance with the anatomic configuration dictated by the lesion.

Other objects, features, and characteristics of the present invention, as well as the methods of operation and functions of the related elements of the structure, and the combination of parts and economics of manufacture, will become more apparent upon consideration of the following description with reference to the accompanying drawings, all of which form a part of this specification.

DETAILED DESCRIPTION OF THE INVENTION

The present invention relates to a radially expandable stent used to open or expand a targeted area in a body lumen. The stent has a generally hollow cylindrical shape with open distal and proximal ends as demonstrated in FIGS. 1 and 7. The cylindrical body comprises a plurality of elongated stent components which are interconnected by means of an interlocking weave-like mechanism. The device is delivered using a percutaneous transluminal catheter device which may or may not incorporate an inflatable balloon used to expand the stent. The stent is designed to permit flexing both radially and longitudinally to conform to the curved body of the applicable lumen.

Figures 1, 2, 4, 6:
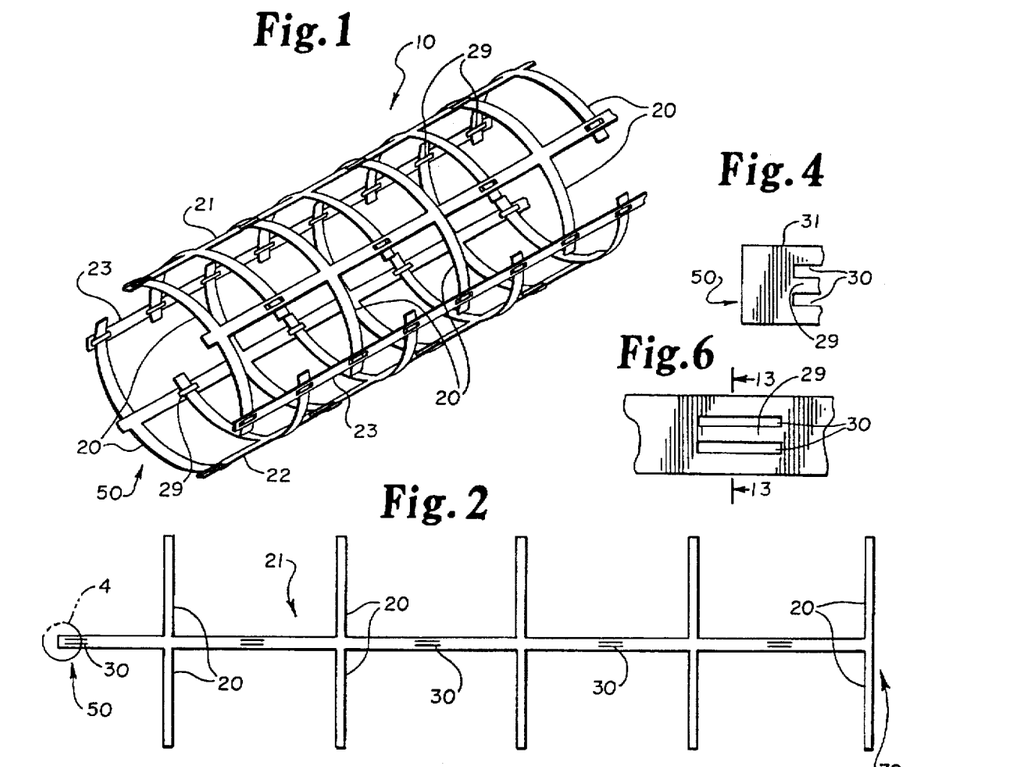
FIG. 1 shows a perspective view of a first embodiment of the invention according to one preferred construction, in its expanded form.
FIG. 2 shows a plan view of a first stent component of the first stent embodiment of FIG. 1.
FIG. 4 shows a detail view of a section of the paired slots at the end of the first stent embodiment of FIG. 1, the view being taken from FIG. 2.
FIG. 6 shows a detail view of the paired slots of the first stent embodiment of FIG. 1, the view being taken from FIG. 3.

The stent that is the subject of this invention incorporates a number of design concepts that utilize the interlocking weave-like configuration. FIG. 1 illustrates one preferred design of the present invention, referred to as the first stent embodiment. The stent, generally designated in FIG. 1, incorporates circumferential members or fingers 20 positioned along elongated stent components, generally designated 21, 22, and 23 (also seen in FIGS. 2, 3, & 5). Upon assembly of these components fingers 20 weave into paired slots 30 positioned along adjacent stent components 21,22 and 23 as shown in FIG. 1. This interlocking system is continued using additional parallel stent components in which the last component is weaved into the first component to form a open ended hollow cylinder construction of appropriate desired diameter as shown in FIG. 1. This continuous interlocking weave-like network radially expands while positioned in the lumen through the use of a balloon to a determined diameter or by use of self-expanding material.

The first stent component 21 shown in FIG. 2 of the first stent embodiment has a longitudinal backbone 31 with a plurality of pairs of opposing circumferential members 10 or fingers extending perpendicular from the backbone 31. Paired slots 30 are positioned along the backbone 31 alternating in position with the circumferential members 20. The paired slots 30 as shown in FIGS. 4 and 6 are parallel to each other and are linear relative to the backbone 31 or the stent component. The backbone of stent component 21 has a proximal end 50 and a distal end 70. The paired slots 30 and the circumferential members 10 alternate along the backbone 31 starting with a paired slot 30 at the proximal end 50 and concludes with a pair or circumferential members 20 at the distal end 70.

Figure 3:
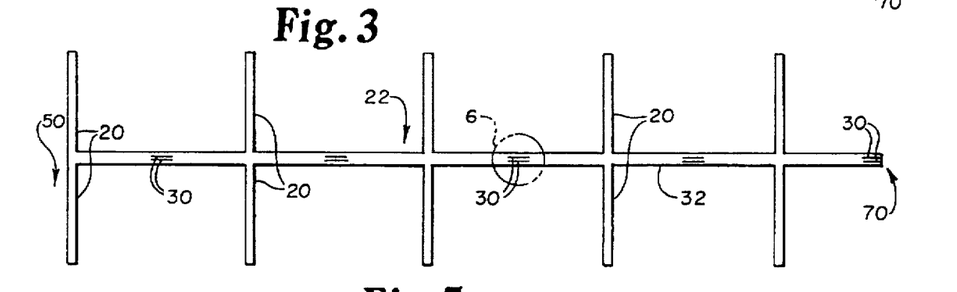
FIG. 3 shows a plan view of a second stent component of the first stent embodiment FIG. 1.

The second stent component, generally designated 22, shown in FIG. 3 is similar in construction to that of stent component 21 except for the order in which the plurality of circumferential members 20 and paired slots 30 are alternately positioned. In stent component 22 the order starts with a pair of circumferential members 20 at the proximal end 50 of backbone member 32 and terminates with a pair of slots 30 at the distal end 70 of stent component 22.

Figure 5:
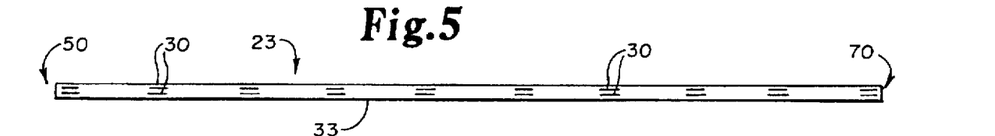
FIG. 5 shows a plan view of a third stent component of the first stent embodiment of FIG. 1.

The third stent component, generally designated 23, illustrated in FIG. 5, also incorporates an elongated backbone 33 with a plurality of paired slots 30 positioned equidistantly along the entire length of the backbone 33. In this particular stent component there are no circumferential members positioned along the backbone.

Combined, these three stent components 21, 22 and 23 incorporate sliding elements to create a cylindrical configuration as shown in FIG. 1. The weaving or interlocking mechanism is achieved by sliding the circumferential members, or fingers 20, of one component through the paired slots 30 of another stent component adjacent to the former in a weave configuration, generally designated as 82 illustrated in FIG. 14. This mechanism enables the stent to expand radially without yielding or plastically deforming the material of which the stent is fabricated. The resulting expanded configuration is best seen in FIG. 1.

In the final construction or assembly as shown in FIG. 1, stent component 21 is positioned adjacent and parallel to stent component 22 and is connected thereto by way of the interconnecting weave-like mechanism 82 formed of elements 20 and 30. Stent component 22 is positioned adjacent and parallel to stent component 23 and connected thereto by means of the interconnecting weave-like 82 mechanism of fingers 20 and slots 30. To close the stent and create the cylindrical shape from the individual components, the opposing circumferential members 20 of stent component 21 are weaved into the paired slots 30 of the stent component 23.

Stent components 21, 22 & 23 form a series of stent components. To enlarge the potential diameter of the stent, another series of the three components may be added in the same manner as the first series has been connected. FIG. 1 illustrates the use of two series of components closed to create the cylindrical shape. Stent component 23 of the final series added would be connected to stent component 21 of the first series to complete the cylindrical stent configuration, this is referred to as "closing" the stent to create the cylindrical shape from the individual parts. The potential diameter of the stent may also be increased by extending the length of the fingers.

Figure 14:
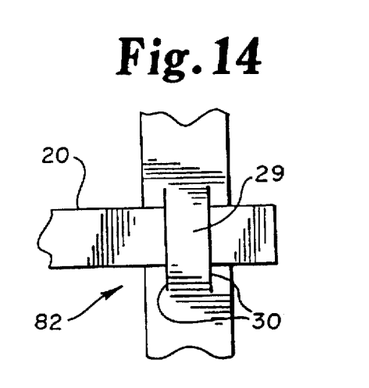
FIG. 14 shows a detail view of a weave-like configuration in which a finger slides through a paired slot used in both the first stent embodiment and second stent embodiment of FIGS. 1 and 7, respectively.

The paired slots 30 dimensions are such that the fingers 20 is held via friction tension or clamping giving a controlled expansion with little or no recoil or collapse. The slot arrangement incorporates multiple parallel paired slots 30 so that the fingers can weave through them providing more control over the sliding movement as shown in FIG. 14. The center portion 29 that lies between the paired slots 30, as illustrated in FIGS. 4 and 6, may be raised or lowered with respect to the plane of the stent component 21, 22 and 23 as shown in FIG. 1. As the center piece 29 between paired slots 30 is raised or lowered, the friction tension diminishes, loosening the weave-like connection 82 and thus allowing the fingers 20 to slide more freely through the paired slots 30. The center piece 29 may be raised or lowered to the extent that the friction tension between the finger 20 and the paired slot 30 is lose enough so as to allow the balloon or expanding means to expand the stent, but tight enough so as to prevent the finger 20 from withdrawing as a result of the stent's own expanding force or to prevent the stent from collapsing under the pressure of the lumen wall.

Once assembled, the assembly forms the cylindrical hollow configuration as seen in FIG. 1 and it can be compressed radially by fully sliding the fingers 20 through the slots 30 for easy insertion into the lumen. The assembly is expanded with either the help of a balloon catheter, by the elastic response of the material used, or both, the weave mechanism 82 allowing for radial expansion without change in longitudinal dimensions of the complete assembly.

Figures 7, 8:
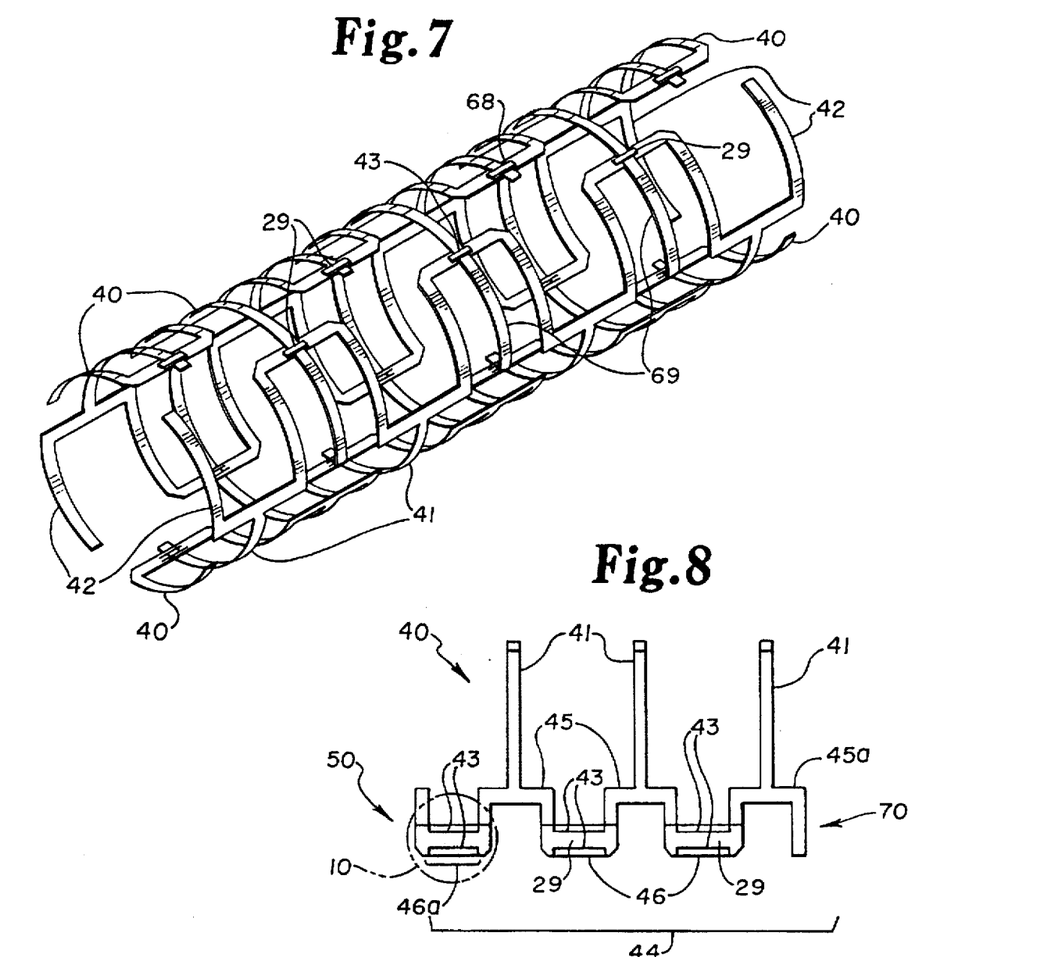
FIG. 7 shows a perspective view of a second embodiment according to another preferred construction of the invention, in its expanded form.
FIG. 8 shows a plan view of a first stent component of the second stent embodiment of FIG. 7.

A second embodiment, sometimes referred to as the second stent embodiment, is shown in FIG. 7. This application of the weave-like mechanism utilizes at least two dissimilar elongated stent components generally designated 40 and 42, shown in FIGS. 8 & 9, respectively, and like the first stent embodiment of FIG. 1 can be expanded to larger diameters by adding additional series of the two components. The two dissimilar stent components 40 and 42, which form a continuous interlocking weave-like network, eventually close to form an open ended cylindrical configuration from the individual components 40 and 42 as shown in FIG. 7. To achieve this closing the fingers 69 of component 42 of the last series used in the construction are inserted into the paired slots 43 of stent component 40 of the first series used in the construction. This particular embodiment radially expands while positioned in the lumen through the use of a balloon to a determined diameter or by use of a self-expanding material. FIG. 7 demonstrates the use of two series of components in a continuous radially expandable weave-like cylinder construction.

Figure 10:
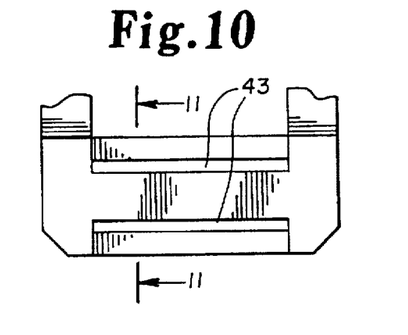
FIG. 10 shows a detail view of the paired slots portion or the second stent embodiment of FIG. 7, taken from FIGS. 8 and 9.

Stent component 40 shown in FIG. 8 has an elongated zig-zag backbone 44 having a set of first edge members 45 linearly arranged and a set of second edge members 46 linearly arranged, the set of first edge members 45 and the set of second edge members 46 being parallel and positioned on opposite sides of the zig-zag backbone 44. A plurality of circumferential members, 41 or fingers extend perpendicular from the first edge members 45 of the zig-zag backbone 44. A plurality of paired slots 43 are positioned along the set of second edge members 46 of the zig-zag backbone 44. The paired slots 43 as shown in FIG. 10 are parallel to each other and are linear relative to the backbone 44. The backbone of stent component 40 has a proximal end 50 and a distal end 70. The second edge members 46 and the first edge members 45 alternate along the backbone starting with edge member 46a at the proximal end 50 and ends with a first edge member 45a at the distal end 70.

Figure 9:
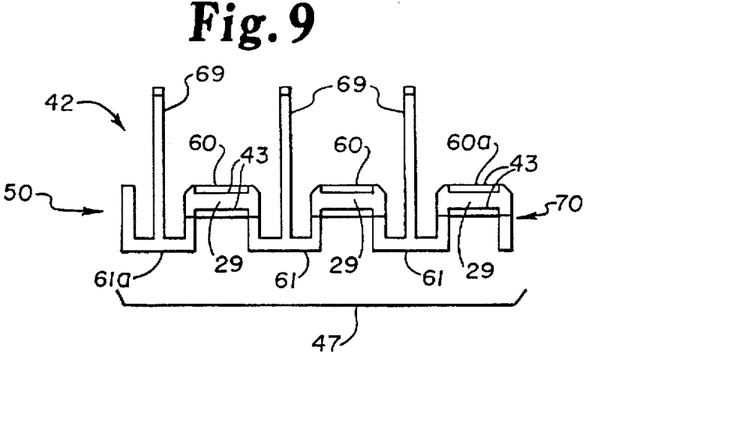
FIG. 9 shows a plan view of a second stent component of the second stent embodiment of FIG. 7.

Stent component 42 shown in FIG. 9 has an elongated zig-zag backbone 47 having a set of first edge members 60 linearly arranged and a set of second edge members 61 linearly arranged, the set of first edge members and the set of second edge members being parallel and positioned on opposite sides of the zig-zag backbone 47. A plurality of circumferential members 69 or fingers extend inwardly and perpendicular from the second edge members 61 of the zig-zag backbone 47. A plurality of paired slots 43 are positioned along the set of first edge members 60 of the zig-zag backbone 47. The paired slots as shown in FIG. 10 are parallel to each other and are linear relative to the backbone of the stent component 42. The backbone of the stent component 42 has a proximal end 50 and a distal end 70. The first edge members 60 and the second edge members 61 alternate along the backbone starting with a second edge member 61a at the proximal end 50 and concludes with a first edge member 60a at the distal end 70.

Combined, these two stent components 40 and 42 incorporate sliding elements 41 and 69 to form a cylindrical configuration as shown in FIG. 7, incorporating at least two of the elongated stent components. The circumferential members or fingers 41 or 69 of one component slide through the paired slots 43 of an adjacent stent component in a weave-like configuration as shown in FIG. 7 enabling the stent to expand radially without yielding or plastically deforming the material of which the stent is fabricated. Stent component 40 is positioned adjacent to the second stent component 42 and compared to component 42 by way of the interconnecting weave-like mechanism of combined slots 43 of stent component 42 and fingers 41.

To close the stent and create the cylindrical shape from the individual components as shown in FIG. 7 the circumferential members 69 of stent component 42 are weaved into the paired slots 43 of stent component 40. To enlarge the diameter potential of the stent, another series, wherein a series consists of stent component 40 and stent component 42, can be added to the first series by connecting stent component 42 of the first series to stent component 40 of the second series. The potential diameter may also be increased by extending the length of the fingers. FIG. 7 illustrates the use of two series of stent components 40 and 42. The stent component 42 of the final series is connected to stent component 40 of the first series thus creating the cylindrical stent formation shown in FIG. 7. This connection is achieved through the weave-like mechanism discussed earlier illustrated in FIG. 14.

Figure 11:
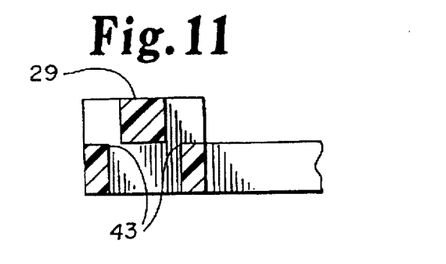
FIG. 11 shows a cross section of a detail view of the paired slots portion of the second stent embodiment of FIG. 7, taken along line 11—11 of FIG. 10.

In both the first stent embodiment and the second stent embodiment the circumferential members or fingers 20, 41 and 69 and the center pieces 29 may be modified to incorporate arresting mechanisms which prevent the disengagement of the fingers from the paired slots 30 and 43 upon expansion, and also may serve to prevent collapse when the friction tension is inadequate. In the absence of, or in conjunction with, arresting mechanisms, the fingers are held in place by friction tension by way of the weave-like connection as shown in FIG. 14. The paired slots 30 and 43 dimensions of the first stent embodiment and the second stent embodiment, respectively, are such that the fingers can be held via friction tension or clamping giving a controlled expansion with little or no recoil or collapse. The center portion 29 that lies between the paired slots 30 and 43, respectively, as illustrated in FIGS. 6 and 10, may be raised or lowered with respect to the plane of the stent components as illustrated in FIGS. 1, 7 and 11. As the center piece 29 is raised or lowered, the friction tension diminishes, loosening the weave-like connection and thus allowing the fingers 20, 41 and 69 to slide more freely through the coordinating paired slots 30 and 43. The center piece 29 is raised or lowered to the extent that the friction tension between the fingers and the paired slots is lose enough so as to allow the balloon or expanding means to expand the stent, but tight enough so as to prevent the finger from withdrawing as a result of the stent's own expanding force or to prevent the stent from collapsing under the pressure of the lumen wall.

Figure 12:
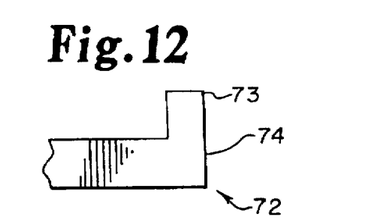
FIG. 12 shows a detail view of a lip arresting mechanism located at the end of a modified circumferential member or finger which may be incorporated in both the first stent embodiment and second stent embodiment of FIGS. 1 and 7, respectively, as an alternative to the straight, flat ends of the circumferential members shown in FIGS. 2, 3, 8 and 9.

Examples of different embodiments of the arresting mechanism are illustrated in FIGS. 12, 13, 15, 16, 17, 18 & 19. This arresting mechanism may be a simple lip arresting mechanism, generally designated 72, as shown in FIG. 12, wherein a lip 73 is positioned at the end 74 of the fingers 20, 41 or 69. The modified finger, which incorporates the simple lip 73, is slid through the corresponding paired slot 30 and 43 allowing the lip to engage the paired slot preventing removal. The fingers may incorporate multiple lip structures along the finger to act as a ratcheting mechanism allowing for greater freedom in setting the potential diameter and as a prevention from collapse of the stent body under the pressure of the vessel.

Figure 13:
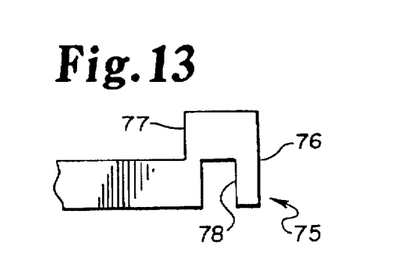
FIG. 13 shows a detail view of a lip and catch arresting mechanism located at the end of a modified circumferential member or finger which may be incorporated in both the first stent embodiment and second stent embodiment of FIGS. 1 and 7, respectively, as an alternative to the straight, flat ends of the circumferential members shown in FIGS. 2, 3, 8 and 9.

A lip and catch arresting mechanism, generally designated 75, as shown in FIG. 13, may also be used. In this alternative mechanism the modified finger 20 & 41 incorporates a lip 77 and catch 78 at the end 76 of the circumferential member as demonstrated in FIG. 13. The lip 77 and catch 78 arrangement allows for the engagement and locking of the paired slots 30 or 43 restricting movement in either direction.

Figure 17:
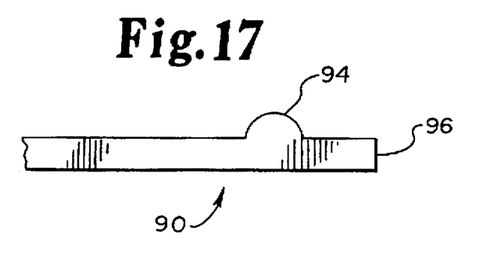
FIG. 17 shows a detail view of an end of a modified circumferential member which acts as a male piece in a dimple or detent arresting mechanism, the female piece of which is illustrated in FIGS. 19 and 18, which may be incorporated in the first and second stent embodiments, respectively, as an alternative to the straight, flat ends of the circumferential members shown in FIGS. 2, 3, 8 and 9.
Figure 18:
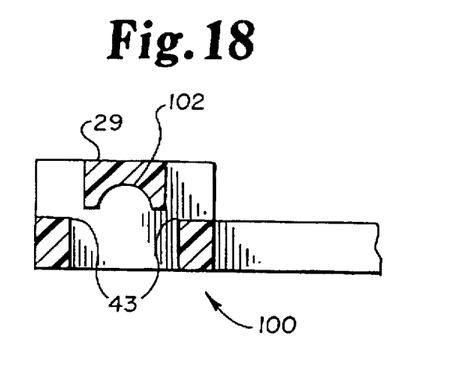
FIG. 18 shows a cross section of a detail view of a modified paired slot which acts as a female portion of a dimple or detent arresting mechanism which may be used in the second stent embodiment of FIG. 7, taken along line 11—11 of FIG. 10.
Figure 19:
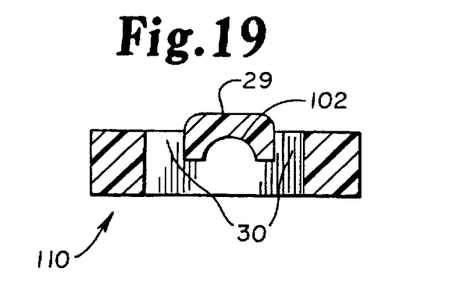
FIG. 19 shows a cross section of the detail view of a modified paired slot which acts as a female portion of a dimple or detent arresting mechanism which may be used in the first stent embodiment of FIG. 1, taken along line 13—13 of FIG. 6.

Another potential arresting mechanism could be a dimple or detent arresting mechanism, the elements of which are illustrated in FIGS. 17, 18 & 19. This arresting mechanism incorporates a male portion, which is a modified circumferential member end, generally designated 90, as shown in FIG. 17, with a raised convex portion 94 positioned toward the end 96 of a circumferential member as shown in FIG. 17. The female portion for the second stent embodiment, generally designated 100, as shown in FIG. 18, is a modified center piece 29 between a paired slot 43. The modified center piece 29 has a dimple 102 or detent positioned on the underside of the center piece 29 between the paired slots 43. The male portion 94 and the female portion 102 form a mating relationship as the finger is withdrawn from the paired slots 43, securing the finger in the corresponding paired slot.

The first stent embodiment may also use this dimple or detent arresting mechanism. In such a mechanism the first stent embodiment uses the modified circumferential member 90 as shown in FIG. 17 for its male portion and a modified center piece 29 between paired slots 30, generally designated 110, as shown in FIG. 19, for its female portion. The modified center piece 29 is raised or lowered slightly and has a dimple 102 or detent positioned on the underside of the center piece 29 between the paired slots 30, as shown in FIG. 19. The male portion 94 and the female portion 102 form a mating relationship as the finger is withdrawn from the paired slots 30, securing the finger in the corresponding paired slot. For both the second stent embodiment and the first stent embodiment the male portion and the female portion may be switched, positioning the male portion on the center pieces 29 and positioning the female portions on the circumferential members.

Figure 20:
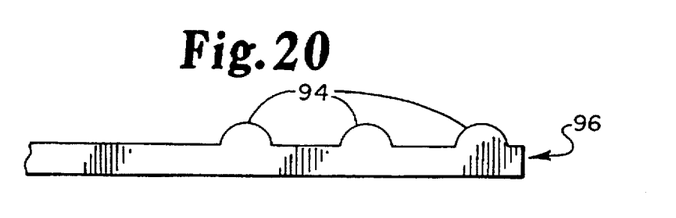
FIG. 20 shows a detail view of an end of a modified circumferential member which acts as a convex arresting mechanism and may be incorporated in the first and second stent embodiments as an alternative to the straight, flat ends of the circumferential members shown in FIGS. 2, 3, 8 and 9.
Figure 21:
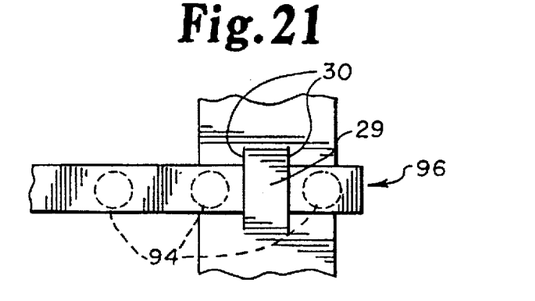
FIG. 21 shows a detail view of a ratcheting arresting mechanism using convex portions which may be used in both the first stent embodiment and second stent embodiment of FIGS. 1 and 7, respectively.

The modified finger shown in FIG. 17 may also be utilized alone as an arresting mechanism. The finger is pushed through the receiving paired slot until the convex portion 94 is exposed on the other side, locking the finger in place. This mechanism prevents the finger from being pulled out, but it depends on friction tension to prevent collapsing of the stent body. FIGS. 20 and 21 illustrate an arresting mechanism that prevents withdrawal of the finger end 96 as well as collapse of the stent. Multiple convex portions 94 may by positioned along the finger creating a rachet mechanism within the paired slot as shown in FIG. 21. This ratcheting mechanism allows for greater freedom in setting the potential diameter, and as a prevention from collapse of the stent body under the pressure of the vessel.

Figure 15:
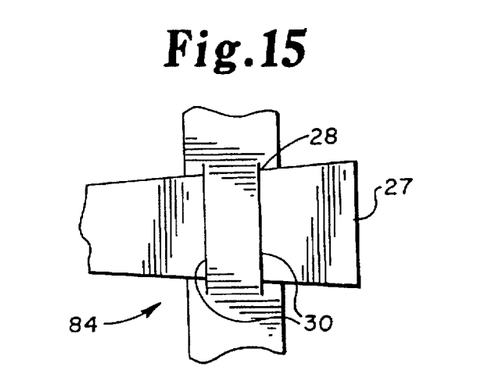
FIG. 15 shows a detail view of a tapered or increased width arresting mechanism arrangement which may be used in both the first stent embodiment and second stent embodiment of FIGS. 1 and 7, respectively.
Figure 16:
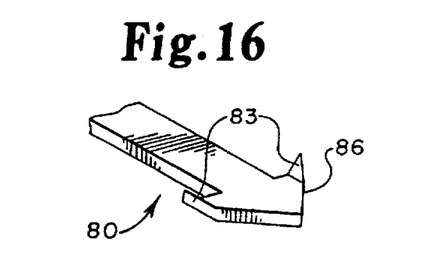
FIG. 16 shows a detail view of an arrowhead arresting mechanism arrangement which may be used in both the first stent embodiment and second stent embodiment of FIGS. 1 and 7, respectively.

FIG. 15 shows still further means by which to arrest the finger in place in the corresponding paired slot. This tapered end arresting mechanism, generally designated 84, as shown in FIG. 15, demonstrates an arresting mechanism in which the end of the circumferential member 20, 41 or 69 increasingly widens 27, creating more resistance within the paired slots 30 of 43 as the finger is withdrawn, eventually stopping the finger in a secure position by wedging 28 it into the pair slot, not allowing further expansion.

Still another arresting mechanism is the arrowhead arresting mechanism, generally designated 80, as shown in FIG. 15. This mechanism incorporates an arrowhead 86, which allows the finger 20, 41 or 69 to slide into the paired slot 30 or 43, but prevents the finger from being withdrawn past a certain point because of the barbs 83 on the arrowhead. The fingers may incorporate multiple arrowhead structures along the finger to act as a ratcheting mechanism allowing for greater freedom in setting the potential diameter and as a prevention from collapse of the stent body under the pressure of the vessel.

These arresting mechanisms can be incorporated anywhere along the length of the finger to let the stent radially expand to a predetermined diameter without allowing the fingers to fully slide out of the corresponding slots. Arresting mechanisms can be positioned to prevent both further expansion and the collapse of the stent.

The weave-like interconnecting mechanism and arresting mechanism in the second embodiment shown in FIG. 7 is accomplished in the same manner as the first embodiment illustrated by FIG. 1, but the configuration of stent component 42 of the second stent embodiment of FIG. 7 will be such that the finger length 69 will be longer than that of the finger 41 length of the stent component 40 and will only incorporate an arresting mechanisms as shown in FIGS. 12, 13, 15, and 16 at the end of the circumferential member 69. Finger 69 incorporates friction tension to secure it in any place along the length of the circumferential member as shown in FIG. 7. This extra length allows for more flexibility within the lumen, expanding to engage the walls of the lumen uniformly along the entire length of the stent. The finger 69 of component 42 is allowed to slide freely through the corresponding paired slot 43 of stent component 40 allowing the stent to expand uniformly through the use of a catheter balloon or self-expanding material. The extra long finger 69 of stent component 42 prevents the weave-like connection 82 from releasing during expansion without limiting the potential diameter. This will ensure that the stent will not have a too small a diameter for the lumen and that future expansion may take place via re-dilatation by a balloon.

The parts for the components for both embodiments may be fabricated from a metal as well as other materials. Indicated metals are Elgiloy alloy, stainless steel, nitinol alloy and biodegradable and nonbiodegradable plastic. A possible parts fabrication method would be to use a photo-etching process. In this process a mask is developed such that when the sheet of material is etched in a reacting solution, such as acid, the masked or protected portions form the stent components. The photo-etching process allows for an accurate fabrication technique and selective etching optimizing part thickness and size. This technique allows for selective half-etching of the slot webs to facilitate finger assembly.

While this invention may be embodied in many different forms, there are described in detail herein specific preferred embodiments of the invention. This description is an exemplification of the principles of the invention and is not intended to limit the invention to the particular embodiments illustrated.

An improvement of the present invention over the prior art is the advantages of the sliding mechanism that allows for uniform stent expansion and the design of the stent components allowing for conforming flexibility. The sliding mechanisms facilitates stent expansion without incorporating plastic deformation. The present stent invention keeps a constant cylindrical shape during radial expansion without altering the shape of the stent elements. The longitudinal size of the stent also remains constant as it expands within the lumen. Whereas previously created stents in the prior art have a tendency to lose their longitudinal or cylindrical shape during radial expansion, the present invention remains consistent in its general configuration both in length and in cylindrical uniformity. The design of the present invention enables the stent to conform to the walls of the lumen without any increase in length or incorporation of plastic deformation while maintaining structural integrity.

A further advantage of the present invention over the prior art is its frame-like construction. This construction allows for adequate support while using minimal material. This is an advantage over the rolled tube-like stent illustrated by the Stack patent, U.S. Pat. No. 5,306,286. It is preferable to have no more than 10–15% of the inner wall covered by the stent itself. The smaller surface area that contacts the inner lumen wall of the present invention allows for greater exposure to blood and other substances essential to the viability of the inner wall of the lumen without losing support.

The zig-zag construction of the second embodiment solves the rigidity problem common among many pieces of prior art. This construction allows the stent more longitudinal flexibility to conform to irregularities in the lumen. Stents such as the Stack stent, U.S. Pat. No. 5,306,286, are constructed using a one piece material rolled over upon itself. This one piece formation limits its longitudinal flexibility causing it to be more stiff and nonconforming to the inner walls of the targeted lumen.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. An expandable stent for implantation within a body lumen comprising:
   a plurality of elongated stent components, wherein the stent components are arranged longitudinally and substantially parallel to each other and have a plurality of slots thereon; and
   a plurality of circumferential members affixed to the stent components,
   wherein the circumferential members of one component are slidably engaged by the slots of an adjacent component forming a generally cylindrical body with open proximal and distal ends.

2. A stent as in claim 1, wherein the circumferential members are substantially perpendicular.

3. A stent as in claim 1, further comprising a plurality of paired slots positioned along the stent components, wherein the circumferential members of one component are slidably received into the paired slots of an adjacent component, whereby the stent is radially expandable to engage the lumen walls by sliding the circumferential members through the paired slots to separate the components from each other diametrically.

4. A stent as in claim 1, wherein the plurality of elongated stent components comprises:
   a first stent component with a longitudinal backbone having a proximal end and a distal end, the first stent component comprising:
      a plurality of opposingly paired circumferential members perpendicularly affixed to the first stent component and spaced therealong; and
      a plurality of paired slots linearly positioned and spaced along the longitudinal backbone of the first stent component, the paired slots and the circumferential members alternating in position relative to each other starting with a paired slot at the proximal end of the first stent component;
   a second stent component with a longitudinal backbone having a proximal end and a distal end, the second stent component comprising:
      a plurality of opposingly paired circumferential members perpendicularly affixed to the second stent component and spaced therealong;
      a plurality of paired slots linearly positioned and spaced along the longitudinal backbone of the second stent component, the paired slots and the circumferential members alternating in position relative to each other starting with a pair of the circumferential members at the proximal end of the second stent component; and
   a third stent component including a longitudinal backbone having paired slots linearly positioned along the longitudinal backbone,
   wherein the circumferential members of one component are slidably received into the paired slots of an adjacent component forming a weave-like interlocking configuration.

5. A stent as in claim 1 wherein the plurality of elongated stent components comprises:
   a first stent component with a zig-zag longitudinal backbone having a set of first edge members linearly arranged and a set of second edge members linearly arranged, the first edge members and the second edge members being parallel and positioned on opposite sides of the zig-zag backbone, the first stent component comprising:
      a plurality of circumferential members extending perpendicular and outwardly from the first edge members of the zig-zag backbone of the first stent member; and
      a plurality of paired slots positioned in the second edge members of the zig-zag backbone of the first stent member, the paired slots being parallel to each other and linear relative to the backbone of the first stent component, the backbone of the first stent component having a proximal end and a distal end, wherein the first edge members and the second edge members alternate in position along the backbone of the first stent component, starting at the proximal end with a second edge member; and
   a second stent component with a zig-zag longitudinal backbone having a set of first edge members linearly arranged and a set of second edge members linearly arranged, the first edge members and the second edge members being parallel and positioned on opposite sides of the zig-zag backbone, the second stent component comprising:
      a plurality of circumferential members extending perpendicular and inwardly from the first edge members of the zig-zag backbone of the second stent component; and
      a plurality of paired slots positioned in the second edge members of the zig-zag backbone of the second stent component, the paired slots being parallel to each other and linear relative to the backbone of the second stent component, the backbone of the second stent component having a proximal end and a distal end, wherein the first edge members and the second edge members alternate in position along the backbone of the second stent component, starting at the proximal end with a first edge member; wherein the circumferential members of the first stent component are slidably receivable into the corresponding paired slots of the second stent component and the circumferential members of the second component are slidably receivable into the corresponding paired slots of the first stent component.

6. An expandable stent for implantation within a body lumen comprising:

a plurality of elongated stent components, wherein the stent components are arranged longitudinally and substantially parallel to each other; and a plurality of circumferential members affixed to the stent components, the circumferential members having a straight linear configuration, wherein the circumferential members of at least two of the components are slidably engaged by an adjacent component forming a generally cylindrical body with open proximal and distal ends.

7. The expandable stent of claim 6, having no more than six elongated stent components.

8. The expandable stent of claim 6, wherein each elongated stent component is releasably engaged to the elongated stent component adjacent thereto.

9. The expandable stent of claim 6, wherein the circumferential members are engaged with the elongated stent components via a plurality of slots in the elongated stent components.

10. The expandable stent of claim 6, wherein the elongated stent components have a zig-zag configuration.

* * * * *

UNITED STATES PATENT AND TRADEMARK OFFICE
CERTIFICATE OF CORRECTION

PATENT NO. : 5,733,328

DATED : March 31, 1998

INVENTOR(S) : Paul J. Fordenbacher

It is certified that error appears in the above-identified patent and that said Letters Patent is hereby corrected as shown below:

Column 5, line 51:   Delete "10" and insert -- 20 --;

Column 5, line 56:   Delete "31 or" and insert -- 31 of --;

Column 5, line 59:   Delete "members 10", and insert -- members 20 --;

Column 8, line 5:    Delete "compared" and insert -- connected --

Column 9, line 64:   Delete "15" and insert -- 16 --.

Signed and Sealed this

Twenty-first Day of July, 1998

Attest:

BRUCE LEHMAN

*Attesting Officer*  *Commissioner of Patents and Trademarks*